United States Patent [19]

Hogan et al.

[11] 4,386,230

[45] May 31, 1983

[54] HYDROCARBON CONVERSION

[75] Inventors: Philip J. Hogan, Runcorn; Allan Stewart, Frodsham; Thomas V. Whittam, Darlington, all of England

[73] Assignee: Imperial Chemical Industries PLC, London, England

[21] Appl. No.: 331,831

[22] Filed: Dec. 17, 1981

[30] Foreign Application Priority Data

Dec. 17, 1980 [GB] United Kingdom ............... 8040396

[51] Int. Cl.$^3$ ............................................. C07C 2/68
[52] U.S. Cl. ................................. 585/467; 585/469; 585/475; 585/640
[58] Field of Search ............... 585/467, 469, 475, 640

[56] References Cited

U.S. PATENT DOCUMENTS 3,957,621 5/1976 Bonacci et al. ...................... 585/475
4,052,476 10/1977 Morrison ............................. 585/471
4,052,479 10/1977 Chang et al. ........................ 585/640
4,097,542 6/1978 Lake ................................... 585/467
4,098,837 7/1978 Chu ..................................... 585/471
4,100,215 7/1978 Chen ................................... 585/467
4,172,856 10/1979 Spencer et al. ..................... 585/640
4,229,608 10/1980 Chen et al. .......................... 585/640
4,238,630 12/1980 Parker ................................. 585/467
4,278,827 7/1981 Chu et al. ............................ 585/467

FOREIGN PATENT DOCUMENTS 5315 6/1975 European Pat. Off. .
1463359 7/1976 United Kingdom .

Primary Examiner—Curtis R. Davis
Attorney, Agent, or Firm—Cushman, Darby & Cushman

[57] ABSTRACT

Hydrocarbons e.g. toluene and oxyhydrocarbons e.g. methanol are converted to other hydrocarbons by being contacted under conversion conditions with a catalyst comprising zeolite Nu-5.

6 Claims, No Drawings

HYDROCARBON CONVERSION

HYDROCARBON CONVERSION

The present invention relates to hydrocarbon conversion processes, including disproportionation of alkylbenzenes, alkylation of alkylbenzenes and conversion of alkanols and/or ethers and/or other oxygenated hydrocarbons to olefins and aromatic hydrocarbons, using a catalyst comprising a new zeolite material. The new zeolite material will be referred to as "zeolite Nu-5" and is described in our copending application Ser. No. 331,832, filed concurrently herewith.

Zeolite Nu-5 has a molar composition expressed by the formula: 0.5 to 1.5 $R_2O$ : $Y_2O_3$ : at least 10 $XO_2$ : 0 to 2000 $H_2O$ wherein R is a monovalent cation or $1/n$ of a cation of valency n, X is silicon and or germanium, Y is one or more of aluminium, iron, chromium, vanadium, molybdenum, arsenic, manganese, gallium or boron, and $H_2O$ is water of hydration additional to water notionally present when R is H, and has an X-ray pattern substantially as set out in Table 1 (as determined by standard technique using copper K$\alpha$ radiation). Table 1 shows X-ray data for zeolite Nu-5. The X-ray pattern is little affected by the type of cation present or by calcination or hydration.

Within the above definition of chemical composition, the number of moles of $XO_2$ is typically in the range 10 to 5000 zeolite Nu-5 appears to be most readily formed in a state of high purity when the number of moles of $XO_2$ is in the range 45 to 100.

TABLE 1

X-ray diffraction data for Nu-5

| As made Nu-5 | | Hydrogen Nu-5 | |
|---|---|---|---|
| dA | 100$I/Io$ | dA | 100$I/Io$ |
| 11.11 | 70 | 11.12 | 85 |
| 10.02 | 41 | 10.04 | 51 |
| 9.96 | 37 | 9.96 | 45 |
| 9.74 | 18 | 9.75 | 20 |
| 9.00 | 3 | 8.95 | 3 |
| 8.04 | 1 | 8.03 | 1 |
| 7.44 | 6 | 7.43 | 4 |
| 7.08 | 3 | 7.08 | 3 |
| 6.71 | 7 | 6.71 | 8 |
| 6.36 | 14 | 6.37 | 15 |
| 5.99 | 15 | 6.01 | 19 |
| 5.70 | 12 | | |
| 5.59 | 13 | 5.58 | 15 |
| 5.13 | 4 | 5.14 | 3 |
| 5.03 | 6 | 5.02 | 5 |
| 4.984 | 8 | 4.984 | 8 |
| 4.623 | 7 | 4.616 | 8 |
| 4.371 | 15 | 4.370 | 14 |
| 4.266 | 15 | 4.266 | 15 |
| 4.095 | 14 | 4.095 | 9 |
| 4.014 | 11 | 4.022 | 12 |
| 3.859 | 100 | 3.859 | 100 |
| 3.821 | 70 | 3.825 | 68 |
| 3.749 | 39 | 3.755 | 32 |
| 3.725 | 54 | 3.731 | 48 |
| 3.643 | 31 | 3.652 | 28 |
| 3.598 | 4 | 3.601 | 4 |
| 3.484 | 7 | 3.484 | 6 |
| 3.358 | 10 | 3.355 | 9 |
| 3.315 | 12 | 3.315 | 11 |
| 3.054 | 12 | 3.054 | 12 |
| 2.994 | 13 | 2.991 | 15 |
| 2.979 | 13 | 2.979 | 12 |
| 2.015 | 8 | 2.015 | 10 |
| 1.996 | 8 | 1.994 | 10 |

This definition includes both freshly prepared zeolite Nu-5 ("freshly prepared" means the product of synthesis and washing, with optional drying, as hereinafter described) and also forms of it resulting from dehydration, and/or calcination, and/or ion exchange. In freshly prepared zeolite Nu-5, R may include an alkali metal cation, especially sodium, and/or ammonium and hydrogen, and usually includes organic compounds as described below. These organic components are hereinafter referred to as A.

Since Nu-5 is a zeolite, the organic component must be physically trapped within the crystal lattice. It can be removed by thermal or oxidative degradation or by displacement by suitable small molecules. This physically trapped material does not constitute part of the composition for the purposes of the definition. Thus a zeolite Nu-5 as made typically has the following molar composition:

0.7 to 1.5 $M_2O$ : 1.0 to 200 A : $Y_2O_3$ : 10 to 5000 $XO_2$ : 0 to 2000 $H_2O$ wherein M is an alkali metal, ammonium or hydrogen.

The $H_2O$ content of freshly prepared zeolite Nu-5 depends on the conditions in which it has been dried after synthesis.

In calcined forms of zeolite Nu-5, R may be any cation including hydrogen since the organic component is burnt out in the presence of air, leaving hydrogen as the other balancing cation, or otherwise displaced prior to calcination.

Among the ion-exchanged forms of zeolite Nu-5 the ammonium ($NH_4^+$) is of importance since it can be readily converted to the hydrogen form by calcination. The hydrogen form can also be prepared directly by exchange with an acid. The hydrogen-form and forms containing metals introduced by ion exchange are described further below.

While the X-ray data for "as made" and hydrogen Nu-5 show a strong similarity to data for ZSM5, there are very significant differences in line intensities in addition to extra lines present in Nu-5. These differences in line intensities are very substantial, and in scanning the spectrum of d-spaces, the intensity variations are very irregular, which suggests the differences between the framework of Nu-5 and ZSM5 is complex. The differences in X-ray data are discussed in our copending application Ser. No. 331,832, filed concurrently herewith wherein significant differences in sorption data are also detailed.

The aforesaid application Ser. No. 331,832, filed concurrently herewith also describes a method of making zeolite Nu-5 which comprises reacting an aqueous mixture comprising at least one oxide $XO_2$, at least one oxide $Y_2O_3$ and at least one compound selected from pentaerythritol, dipentaerythriol and tripentaerythritol.

The reaction mixture preferably has the following molar composition:

| $XO_2/Y_2O_3$ | 10 to 5000 | preferably 50 to 200 |
|---|---|---|
| $MOH/XO_2$ | 0.01 to 0.5 | preferably 0.10 to 0.25 |
| $Z^-/Y_2O_3$ | 0 to 5000 | preferably 10 to 100 |
| $A/Y_2O_3$ | 1 to 200 | preferably 1 to 50 |
| $H_2O/XO_2$ | 10 to 500 | preferably 15 to 300 | where X is silicon and/or germanium, Y is one or more of aluminium, gallium, iron, chromium, vanadium, molybdenum, arsenic, manganese, or boron, M is an alkali metal or ammonium, and A is the aforesaid pentaerythritol compound. $Z^-$ is a strong acid radical present as a salt of M and may be added as a free acid to reduce the free $OH^-$ level to a desired value. M can be present as hydroxides or salts of inorganic or organic acids provided the MOH/XO$_2$ requirement is fulfilled.

The preferred pentaerythritol compound is pentaerythritol itself, and the preferred acid radical is sulphate.

The preferred alkali metal (M) is sodium. The preferred oxide XO$_2$ is silica (SiO$_2$) and the preferred oxide Y$_2$O$_3$ is alumina (Al$_2$O$_3$).

According to one aspect of the present invention we provide a hydrocarbon conversion process which comprises contacting an alkylbenzene, under disproportionation conditions in the vapour or liquid phase with a catalyst comprising zeolite Nu-5.

Suitable alkylbenzene starting materials include toluene, ortho-, meta- and para- xylenes, ethylbenzene, trimethylbenzene, tetramethylbenzene and the like, or mixtures thereof.

The disproportionation process according to the invention is particularly applicable to the disproportionation of methylbenzenes, and more particularly to the disproportionation of toluene to give a product comprising ortho-, meta- and para- xylenes and benzene. The disproportionation process is especially applicable to the selective production of para-xylene from toluene, the said para-xylene being obtained in excess of its normal equilibrium concentration (which is about 23-24%) of the xylene isomers.

Such a process is effectively carried out at a temperature between about 400° C. and about 750° C., at a pressure of between 1 atmosphere abs and 60 atmospheres abs, utilising a weight hourly space velocity (WHSV) of between about 1 and about 20, wherein WHSV signifies kg. of feed per kg. of catalyst per hour.

The effluent from the reaction is separated and distilled to remove the desired products, e.g. p-xylene, and unreacted product may be recycled for a further reaction.

According to another aspect of the present invention we provide a hydrocarbon conversion process which comprises contacting an alkylbenzene or a mixture of alkylbenzenes and an alkylating agent under alkylating conditions in the vapour or liquid phase with a catalyst comprising zeolite Nu-5.

The alkylbenzene starting materials include toluene, ortho-, meta- and para- xylenes, ethylbenzene, trimethylbenzene, tetramethylbenzene, and the like, or mixtures thereof. The alkylating process of the invention is especially applicable to the use of toluene as the starting material.

Suitable alkylating agents include alkanols, alkyl halides, alkyl ethers, alkyl sulphides and olefins. Preferred methylating agents include methanol, methyl chloride, methyl bromide, methyl carbonate, dimethyl ether and dimethyl sulphide. The use of methanol as the methylating agent is especially preferred.

The molar ratio of the alkylating agent to the alkylbenzene is generally between about 0.05 and about 5, for example between about 0.1 and about 3.

An especially preferred alkylating process according to the invention comprises the methylation of toluene using methanol as the methylating agent to give a product comprising the xylene isomers, and in particular to a process for the selective production of para-xylene from toluene and methanol, the said para-xylene being obtained in excess of its normal equilibrium concentration (which is about 23-24%) of the xylene isomers.

The methylation process is suitably carried out at a temperature in the range of about 250° to about 750° C. preferably about 400° to about 600° C., at a pressure between 1 atmosphere abs and about 60 atmosphere abs and at a WHSV of 1 to about 1500.

Another especially preferred alkylation process comprises the alkylation of toluene with an olefin, for example ethylene, producing an alkyltoluene. This process is suitably carried out at a temperature between about 200° C. and about 750° C., at a pressure of between 1 atmosphere abs and 60 atmospheres abs, and utilising a WHSV of 0.08 to about 20.

According to a still further aspect of the present invention we provide a process for the production of hydrocarbons which comprises contacting an alcohol and/or ether, and/or other oxygenated hydrocarbons under conversion conditions with a catalyst comprising zeolite Nu-5.

The starting material is preferably a lower monohydric alcohol having up to four carbon atoms, their ether derivatives or mixtures thereof. Suitable alcohol starting materials include methanol, ethanol, n-propanol, isopropanol, n-butanol, sec-butanol and iso-butanol. Suitable ether starting materials include ethers derived from the aforesaid alcohols and include both symmetrical ethers (e.g. dimethyl ether) and unsymmetrical ethers (e.g. methyl-ethyl ether). It is particularly preferred to use methanol and/or dimethyl ether as the starting material(s).

The process is suitably carried out at a temperature in the range from 250° C. to 700° C., and preferably in the range 350° C. to 500° C.

The pressure at which the process is carried out is suitably in the range 0.2 to 50 atm abs, preferably 0.5 to 20 atm abs.

The weight hourly space velocity (WHSV) is typically in the range of about 0.5 to 50, preferably about 1.0 to 10.0.

The products of the reaction include lower olefins e.g. C$_2$ to C$_7$ olefins, especially ethylene and propylene, and aromatic hydrocarbons, e.g. monocyclic hydrocarbons such as benzene, toluene and xylene.

In the aforesaid conversion processes according to the invention, the catalyst can be prepared from zeolite Nu-5 by ion exchange or impregnation with cations, or oxides, selected from the following, Cu, Ag, Mg, Ca, Sr, Zn, Cd, B, Al, Sn, Pb, V, P, Sb, Cr, Mo, W, Mn, Re, Fe, Co, Ni, noble metals and lanthanides. The catalyst may be in the form of a fixed bed, fixed fluid bed or it may be of the transport bed type.

The catalyst as used maintains its activity for a substantial period, but can be regenerated by heating. For example, when the catalyst is used in the form of a fluidised bed, the catalyst may be continuously withdrawn, passed through a regeneration zone and returned to the reaction.

The invention is illustrated by the following Examples.

EXAMPLE 1

This example illustrates the use of HNu-5 as a catalyst in toluene disproportionation.

Sodium pentaerythritol Nu-5 was prepared as follows:

The synthesis mixture had the following molar composition:

23.9 Na$_2$O, 20 A, Al$_2$O$_3$, 89 SiO$_2$, 3600 H$_2$O, 15.9 SO$_4{}^{2-}$ 30 g pentaerythritol were dispersed in 189 g Q. 79 water-glass (Na$_2$O, 0.01 Al$_2$O$_3$, 3.77 SiO$_2$, 24 H$_2$O) and 300 g water. Next a solution of 5.3 g aluminium sulphate ($Al_2O_3$, 3 $SO_3$, 16 $H_2O$) and 14.8 g 98% sulphuric acid in 304 g water were added with vigorous stirring. The resulting slurry was reacted for 48 hours at 180° C. in a stirred stainless steel 1 liter autoclave, under autogenous pressure. After cooling to 60° C., the slurry was filtered and washed with two liters of distilled water, and dried overnight at 120° C. The product was sodium pentaerythritol Nu-5 having the X-ray diffraction data given in Table 1 and a composition:
0.31 $Na_2O$, 4.7A, $Al_2O_3$, 68 $SiO_2$, 24.6 $H_2O$ The aforesaid Nu-5 product was calcined in air at 450° C. for 16 hours, exchanged with N/10 hydrochloric acid solution and further calcined for 16 hours at 450° C. in air.

About 2 g of the HNu-5 zeolite resulting from these treatments was compressed, crushed and sieved. 0.4855 g of 250–500μ particle size HNu-5 thus prepared was tested for its ability to catalyse toluene disproportionation. The catalyst sample was loaded into a microreactor which was then flushed with nitrogen for 16 hours before the temperature was raised to 530° C. Toluene reactant was then fed to a vaporiser using a peristaltic pump and toluene vapour was passed over the catalyst. The product stream from the reactor was passed through an on-line gas-sampling valve which directed a sample to gas-chromatographic equipment at different times during the reaction. This equipment was capable of estimating toluene conversion and the proportion of p-xylene present in the xylenes fraction in the product stream. The results of this reaction were summarised in Table 2 below for a reaction temperature of 530° C. and a WHSV of 8.9 for the toluene reactant. The reactor operates at approximately atmospheric pressure.

TABLE 2

| On-line Sample No. | Time on Stream (hrs) | Toluene Conversion wt % | wt % p-xylene in xylenes | xylenes wt % | $C^{8+}$ Aromatics wt % |
|---|---|---|---|---|---|
| 1 | 4.5 | 37.7 | 26.0 | 21.3 | 0.5 |
| FLUSHED WITH $N_2$ FOR 16 HOURS AT 530° C. | | | | | |
| 2 | 2.5* | 2.0 | 68.0 | 1.0 | 0 |
| CALCINED IN AIR 100 $cm^3m^{-1}$ 530° C., 2 DAYS | | | | | |
| FLUSHED WITH $N_2$ FOR 1 HOUR AT 530° C. | | | | | |
| 3 | 0.1* | 32.6 | 27.7 | 16.5 | 0.2 |
| 4 | 6.1* | 14.4 | 42.0 | 7.2 | 0.1 |
| FLUSHED WITH $N_2$ FOR 16 HOURS AT 530° C. | | | | | |
| 5 | 1.2* | 4.1 | 52.2 | 2.0 | 0 |

*After recommencement of toluene flow following $N_2$ flush

It will be evident from Table 2 that the amount of p-xylene in the xylenes fraction was in excess of the normal equilibrium concentration of about 24%.

EXAMPLE 2

This example illustrates the use of HNu-5 as a catalyst in toluene methylation.

Zeolite HNu-5 was prepared as described in Example 1.

Approximately 2 g of HNu-5 was compressed, crushed and sieved. 0.537 g of 250–500μ HNu-5 catalyst particles were loaded into a microreactor in which the zeolite was tested for toluene methylation with methanol as methylating agent. Prior to contact with reactants, the catalyst bed was flushed with nitrogen at 500° C. for about 1 hour. A feed consisting of toluene and methanol in a 1:1 molar ratio was passed over the catalyst at 518° C. at a WHSV of 6.2. The results of the reaction are shown in Table 3 below for a sample collected by condensation of the product stream over the time given.

TABLE 3

| Time on Stream (hrs) | Conversion of Toluene wt % | wt % p-xylene in xylenes fraction |
|---|---|---|
| 6.5–7.75 | 30.0 | 44.6 |

It will be evident that the amount of p-xylene in the xylenes fraction was higher in this example than the equilibrium concentration of about 24%.

EXAMPLE 3

This example illustrates the use of HNu-5 as a catalyst in toluene disproportionation.

Sodium pentaerythritol Nu-5 was prepared as follows:

Two solutions were prepared, viz.
Solution A
189 g Q 79 sodium silicate solution
300 g deionised water
30 g pentaerythritol
Solution B
5.3 g aluminium sulphate ($Al_2O_3$. 3 $SO_3$. 16 $H_2O$)
14.8 g concentrated sulphuric acid
304 g deionised water Solution A was introduced into a one liter 316 stainless steel autoclave equipped with an air driven magnedrive turbine stirrer (manufactured by Autoclave Engineers). The autoclave had been cleaned before use by stirring overnight under autogenous pressure at 160° C. with M. sodium hydroxide solution. Solution B was added with stirring at ambient temperature until a homogeneous gel was produced. After sealing the autoclave, the reaction mixture was maintained under autogenous pressure with stirring (ca. 1000 rpm) at 180° C. for 24 hours. At the end of this time, the reaction mixture was cooled to room temperature and the product was filtered and washed with deionised water (3 liters) and dried for several hours at 150° C. to give sodium pentaerythritol Nu-5. The hydrogen form of this zeolite was obtained by calcining the above material at 550° C. for 16 hours in air. After calcination, the material was allowed to cool to room temperature and slurried with 5 $cm^3$ of molar hydrochloric acid solution per gram of zeolite for 16 hours. This exchanged material was filtered, thoroughly washed with deionised water and finally calcined at 550° C. in air for 16 hours. The HNu-5 zeolite powder thus obtained, was compressed, crushed and sieved. Material of 250–500μ particle size was tested for its ability to disproportionate toluene. 0.5976 g of this catalyst was placed in a reactor which was then flushed with nitrogen for one hour as the temperature was raised to 450° C. and for a further hour as the temperature was raised to 528° C.

When the flow of nitrogen was stopped, toluene reactant was fed to a vaporiser using a peristaltic pump and the reaction was carried out and monitored in a similar fashion to Example 1. Toluene conversion and the selectivities to the products were measured and the results are summarised in Table 4 below for toluene disproportionation at 528° C.

TABLE 4

| On-line Sample No. | Time on stream (hrs) | WHSV | Toluene Conversion % | % p-xylene in xylenes | xylenes wt % | $C^{8+}$ Aromatics wt % |
|---|---|---|---|---|---|---|
| 1 | 0.2 | 7.1 | 31.1 | 29.4 | 15.3 | 0.3 |
| 2 | 3.5 | 7.1 | 15.8 | 41.2 | 7.9 | 0.1 |
| FLUSHED WITH $N_2$ FOR 16 HOURS AT 528° C. | | | | | | |
| 3 | 1.2* | 7.1 | 5.0 | 51.0 | 2.5 | 0.0 |
| CALCINED IN AIR AT 100 $cm^3m^{-1}$ AT 528° C., 16 HOURS | | | | | | |
| FLUSHED WITH $N_2$ FOR 0.25 HOUR BEFORE TOLUENE FLOW | | | | | | |
| 4 | 1.4* | 7.1 | 27.5 | 33.8 | 13.6 | 0.3 |
| 5 | 4.0* | 7.1 | 9.3 | 49.0 | 4.6 | 0.0 |

*after recommencement of toluene flow following $N_2$ flush

When the flow of nitrogen was stopped, toluene reactant was fed to a vaporiser using a peristaltic pump and the reaction was monitored in a similar fashion to Example 1. Toluene conversion and selectivity to the various products were measured and the results are summarised in Table 5 below for toluene disproportionation at 528° C.

TABLE 5

| On-line Sample No. | Time on stream (hrs) | WHSV | Toluene Conversion % | % p-xylene in xylenes | xylenes wt % | $C^{8+}$ Aromatics wt % |
|---|---|---|---|---|---|---|
| CALCINED IN AIR AT 100 $cm^3m^{-1}$ AT 528° C., 16 HOURS | | | | | | |
| FLUSHED WITH $N_2$ FOR 0.25 HOUR PRIOR TO TOLUENE FLOW | | | | | | |
| 1 | 0.1 | 7.65 | 12.6 | 55.8 | 6.3 | 0.1 |
| 2 | 2.3 | 7.65 | 4.2 | 61.9 | 2.1 | 0.0 |
| 3 | 0.1* | 7.65 | 24.5 | 43.6 | 11.5 | 0.4 |
| 4 | 1.3* | 7.65 | 17.3 | 52.4 | 8.4 | 0.2 |
| 5 | 0.1* | 7.65 | 21.1 | 50.6 | 10.0 | 0.3 |
| 6 | 2.4* | 7.65 | 7.0 | 67.9 | 3.5 | 0.0 |
| 7 | 0.1* | 7.65 | 21.5 | 48.2 | 10.5 | 0.3 |

*after recommencement of toluene flow following $N_2$ flush

It will be evident that the amount of p-xylene in the xylenes fraction was in excess of the normal equilibrium concentration of approximately 23–24% of the xylenes fraction.

EXAMPLE 4

This example illustrates the use of HNu-5 impregnated with magnesium acetate and treated to yield a catalyst or toluene disproportionation.

Zeolite HNu-5 prepared as described in Example 3, was impregnated with a solution of magnesium acetate in the following manner. 0.32 g magnesium acetate was dissolved in the minimum quantity of deionised water and this was added to 2 g of the sample of HNu-5 which had just been wetted with enough deionised water to form a suspension. After thorough mixing, the mixture was placed in a vacuum oven set at 100° C. and dried down to dryness with pumping. The dry sample was then calcined in air at 450° C. for 16 hours before being compressed, crushed and sieved to yield enough material of 200–250μ particle size to test for toluene disproportionation.

0.5 g of the impregnated zeolite prepared in the above manner was loaded into a reactor which was then flushed with nitrogen for one hour as the temperature was raised to 450° C. and for a further hour during which the temperature was increased to 528° C.

It will be evident that for particular levels of toluene conversion given in the above Table 5, the p-xylene part of the xylenes fraction was in excess of the values found for catalysts by the H form of this preparation as given in Example 3, Table 4. Clearly, impregnation and/or treatment with magnesium acetate has improved the yield of p-xylene at a particular conversion level.

EXAMPLE 5

This example illustrates the use of HNu-5 treated with a lanthanum compound as a catalyst in toluene disproportionation.

Zeolite HNu-5 prepared as described in Example 3 was treated with a solution of lanthanum nitrate in the following manner. Approximately 2 g of the hydrogen form was contacted for 2 days with 100 $cm^3$ of a solution containing 5% by weight lanthanum nitrate. The solid was then filtered off and washed with deionised water before drying at 120° C. for 1.5 hours. The dry solid was then calcined for 16 hours at 450° C.

0.4466 g of 250–500μ particle size material, sieved from the compressed and crushed sample as described previously in previous examples for samples of HNu-5 and treated Nu-5, was tested for toluene disproportionation following the procedure described for catalytic testing for this reaction in Example 1. The results are given in Table 6.

TABLE 6

| On-line Sample No. | Time on stream (hrs) | WHSV | Toluene Conversion % | % P-xylene in xylenes | xylenes wt % | $C^{8+}$ Aromatics wt % |
|---|---|---|---|---|---|---|
| 1 | 0.1 | 9.56 | 27.5 | 35.2 | 13.6 | 0.8 |
| 2 | 2.3 | 9.56 | 9.7 | 56.5 | 4.8 | 0.0 |
| CALCINED IN AIR AT 100 $cm^3m^{-1}$ AT 527° C., 16 HOURS | | | | | | |
| FLUSHED WITH $N_2$ FOR 0.25 HOURS BEFORE TOLUENE FLOW | | | | | | |
| 3 | 0.1* | 9.56 | 22.4 | 45.8 | 10.8 | 0.3 |

TABLE 6-continued

| On-line Sample No. | Time on stream (hrs) | WHSV | Toluene Conversion % | % P-xylene in xylenes | xylenes wt % | C8+ Aromatics wt % |
|---|---|---|---|---|---|---|
| 4 | 2.3* | 9.56 | 11.6 | 59.0 | 5.8 | 0.0 |

*after recommencement of toluene flow following $N_2$ flush

It will be evident that the amount of p-xylene in the xylenes fraction is higher in this example than for the same level of conversion in Example 1 for reaction using the H form as catalyst.

EXAMPLE 6

This example illustrates the use of HNu-5 as a catalyst in toluene disproportionation.

Zeolite HNu-5 was prepared as described in Example 3 with the exception that after adding solution B with stirring to solution A, a further 100 g deionised water was added with stirring. After sealing the autoclave, the reaction mixture was maintained under autogenous pressure with stirring (ca 1000 rpm) at 180° C. for 4 days.

The HNu-5 zeolite powder thus obtained was compressed, crushed and sieved. Material of 250–500μ particle size was tested for its ability to disproportionate toluene. 0.4824 g of this catalyst was placed in a reactor which was then flushed with nitrogen for one hour as the temperature was raised to 450° C. and for a further hour as the temperature was raised to 529° C.

When the flow of nitrogen was stopped, toluene reactant was fed to a vaporiser using a peristaltic pump and the reaction was carried out and monitored in a similar fashion to Example 1. Toluene conversion and the selectivities to the products were measured and the results are summarised in Table 7 below for toluene disproportionation at 529° C.

It will be evident from Table 7 that the amount of p-xylenes fraction is considerably higher than the equilibrium concentration of 24%.

EXAMPLE 7

This example illustrates the use of HNu-5 as a catalyst in toluene methylation.

TABLE 7

| On-line sample No. | Time on stream (hrs) | Toluene Conversion % | wt % p-xylene in xylenes | Xylenes wt % | C8+ Aromatics wt % |
|---|---|---|---|---|---|
| 1 | 0.1 | 21.2 | 46.7 | 10.3 | 0.3 |
| 2 | 2.5 | 12.9 | 58.6 | 6.4 | 0.1 |
| 3 | 4.5 | 6.1 | 71.2 | 3.0 | 0.0 |

Approximately 2 g of the calcined product of Example 6 was compressed, crushed and sieved. 0.524 g of 250–500μ HNu-5 catalyst particles were loaded into a microreactor in which the zeolite was tested for toluene methylation with methanol as methylating agent. Prior to contact with reactants, the catalyst bed was flushed with nitrogen at 527° C. for about one hour. A feed consisting of toluene and methanol in a 1:1 molar ratio was passed over the catalyst at 527° C. at a WHSV of 6.35. The results of such reaction are shown in Table 8 below.

TABLE 8

| Time on stream (hrs) | Conversion of Toluene wt % | wt % p-xylene in xylenes fraction |
|---|---|---|
| 0–1.3 | 21.5 | 62.9 |

TABLE 8-continued

| Time on stream (hrs) | Conversion of Toluene wt % | wt % p-xylene in xylenes fraction |
|---|---|---|
| 1.3–2.3 | 9.8 | 59.9 |

It will be evident that the amount of p-xylene in the xylenes fraction was higher in this example than the equilibrium concentration of about 24%.

EXAMPLE 8

This example demonstrates the use of HNu-5 as a catalyst for methanol conversion to hydrocarbons.

The sample of catalyst in Example 1 was regenerated for 2.5 days in the microreactor by passing air at approximately 60 $cm^3 m^{-1}$ over the catalyst bed which was maintained at 459° C. Prior to introduction of methanol reactant the reactor was flushed with nitrogen at 459° C. for one hour. Methanol was then passed after vaporisation over the catalyst at a WHSV of approximately 6.2 and a reaction temperature of 459° C. After one hour of reaction, the product stream was analysed by on-line sampling. The hydrocarbon distribution of this on-line sample was found to be as described in Table 9 below at complete conversion of methanol (and dimethyl ether).

TABLE 9

| Product | Hydrocarbon distribution wt % |
|---|---|
| Methane | 5.2 |
| Ethylene | 9.1 |
| Ethane | 0.5 |
| Propylene | 17.6 |
| Propane | 9.4 |
| $C_4$ fraction | 26.4 |
| $C_5$ fraction | 10.8 |
| $C_6^+$ non-aromatics | 4.0 |
| Benzene | 0.8 |
| Toluene | 4.4 |
| Ethylbenzene, p and m-xylene | 8.2 |
| o-xylene | 1.6 |
| $C_9^+$ aromatics | 2.0 |
| | 100.0 |

Over the following 1.25 hours on line, the products of the reaction were trapped. Of the 4.1 g of methanol fed in this time 4.0 g of product were trapped, of which 2.3 g were water and 1.7 g hydrocarbons. This would represent 97 wt% recovery of the material fed as trapped water and hydrocarbons and the amount of water collected amounts to 56 wt% of the methanol fed or 57.5 wt% of the product trapped. Conversion of methanol (and dimethyl ether) to products was complete over the period of collection.

What we claim is:

1. A method for the preparation of hydrocarbons which comprises contacting a hydrocarbon or oxyhydrocarbon under conversion conditions with a catalyst comprising zeolite Nu-5.

2. A method according to claim 1 wherein an alkylbenzene is contacted under disproportionation conditions in the vapour or liquid phase with a catalyst comprising zeolite Nu-5.

3. A method according to claim 2 wherein toluene is disproportionated to give a product comprising xylenes and benzene.

4. A method according to claim 1 wherein an alkylbenzene and an alkylating agent are contacted under alkylating conditions in the vapour or liquid phase with a catalyst comprising zeolite Nu-5.

5. A method according to claim 4 wherein the alkylbenzene is toluene.

6. A method according to claim 4 or claim 5 wherein the alkylating agent is methanol.

* * * * *